US010874711B2

(12) United States Patent
Blankenberg

(10) Patent No.: US 10,874,711 B2
(45) Date of Patent: Dec. 29, 2020

(54) USE OF ANNEXIN V TO REDUCE THE SPREAD OF INTRACELLULAR PATHOGENS

(71) Applicant: The Board of Trustees of the Leland Stanford Junior University, Stanford, CA (US)

(72) Inventor: Francis Gerard Blankenberg, Portola Valley, CA (US)

(73) Assignee: The Board of Trustees of the Leland Stanford Junior University, Standford, CA (US)

( * ) Notice: Subject to any disclaimer, the term of this patent is extended or adjusted under 35 U.S.C. 154(b) by 0 days.

(21) Appl. No.: 16/026,513

(22) Filed: Jul. 3, 2018

(65) Prior Publication Data

US 2019/0008922 A1 Jan. 10, 2019

Related U.S. Application Data

(60) Provisional application No. 62/528,691, filed on Jul. 5, 2017.

(51) Int. Cl.

| | |
|---|---|
| *A61K 38/17* | (2006.01) |
| *A61K 51/08* | (2006.01) |
| *C07K 14/47* | (2006.01) |
| *A61P 31/04* | (2006.01) |
| *A61P 31/12* | (2006.01) |
| *A61P 33/02* | (2006.01) |
| *A61K 45/06* | (2006.01) |
| *A61K 9/00* | (2006.01) |

(52) U.S. Cl.

CPC .......... *A61K 38/1709* (2013.01); *A61K 45/06* (2013.01); *A61P 31/04* (2018.01); *A61P 33/02* (2018.01); *A61K 9/0019* (2013.01); *A61K 2300/00* (2013.01)

(58) Field of Classification Search

None

See application file for complete search history.

(56) References Cited

U.S. PATENT DOCUMENTS

| | | | |
|---|---|---|---|
| 2004/0096467 A1 | 5/2004 | Kalden et al. | |
| 2005/0059587 A1 | 3/2005 | Herrmann et al. | |
| 2006/0057591 A1* | 3/2006 | Pryzdial | C07K 16/18 435/6.16 |

FOREIGN PATENT DOCUMENTS

| | | | |
|---|---|---|---|
| WO | 2016/054574 A1 | 4/2016 | |
| WO | WO-2016059146 A1 * | 4/2016 | A61K 38/1709 |

OTHER PUBLICATIONS

Foller et al., "Induction of Suicidal Erythrocyte Death by Listeriolysin from Listeria monocytogenes," Cell. Physiol. Biochem. 20:1051-1060 (2007) (Year: 2007).*

Barsig et al., "The mechanism of cell death in Listeria monocytogenes-infected murine macrophages is distinct from apoptosis", Infect Immun., Oct. 1997, pp. 4075-4081, vol. 65 No. 10, American Society for Microbiology, Washington DC.

Callahan et al., "Phosphatidylserine on HIV Envelope Is a Cofactor for Infection of Monocytic Cells", J Immunol., May 1, 2003, pp. 4840-4845, vol. 170, Issue 9,The American Association of Immunologists, Inc., Rockville, MD.

Crauwels et al., "Apoptotic-like Leishmania exploit the host's autophagy machinery to reduce T-cell-mediated parasite elimination", Autophagy, Mar. 24, 2015, pp. 285-297, vol. 11, Issue 2, Taylor & Francis Group, Abingdon, United Kingdom.

Rupp et al., "Chlamydia pneumoniae hides inside apoptotic neutrophils to silently infect and propagate in macrophages", PLoS One, Jun. 23, 2009, pp. 1-8, e6020, vol. 4, Issue 6, PLoS, San Francisco, CA.

* cited by examiner

*Primary Examiner* — Julie Ha

*Assistant Examiner* — Kristina M Hellman

(74) *Attorney, Agent, or Firm* — Pamela J. Sherwood; Bozicevic, Field & Francis LLP

(57) ABSTRACT

Methods are provided for treating a subject with for an intracellular pathogen infection, by administering an agent that masks or otherwise blocks phosphatidylserine on the pathogen cell surface.

8 Claims, 4 Drawing Sheets
(4 of 4 Drawing Sheet(s) Filed in Color)

Annexin V treated 2 mg/kg/day ip
Starting on Day 1 after Listeria Infection

Untreated Control / Listeria Infection

Untreated Controls (4 x10$^5$ cfu of Listeria injected Day 0)

Annexin V Treated 2 mg/kg ip starting on Day 0
($4 \times 10^5$ cfu of Listeria injected Day 0)

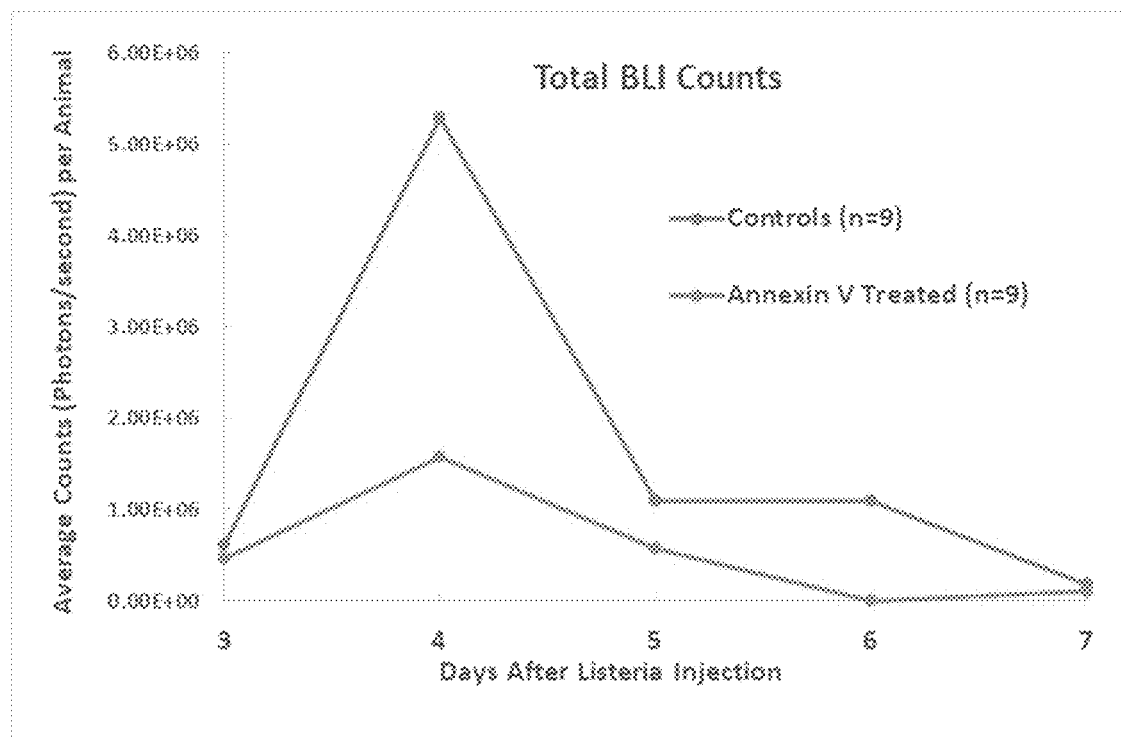
Figure 4. Total BLI Counts (#Photons collected over 30 seconds)

USE OF ANNEXIN V TO REDUCE THE SPREAD OF INTRACELLULAR PATHOGENS

CROSS REFERENCE

This application claims benefit of U.S. Provisional Patent Application No. 62/528,691, filed Jul. 5, 2017, which application is incorporated herein by reference in its entirety.

BACKGROUND

Programmed cell death (PCD) and phagocytic cell removal are a process for multicellular organisms to clear cells, for example during differentiation. These biochemical events leads to characteristic cell changes and death. Phosphatidylserine (PS) exposure on the surface of apoptotic cells, apoptotic bodies and/or vesicles is a major immunosuppressive signal for immune cells as is mediated by a variety of PS receptors. PS also serves as an important factor in the phagocytosis of apoptotic cells, apoptotic bodies and/or vesicles intracellular trafficking of the phagosome for degradation; and is another pathway for the induction of an anti-inflammatory response. Both these PS mediated processes are required to physiologically remove unwanted cells and vesicles from the body without inciting a deleterious immune response as part of normal homeostasis.

The process of an apoptosis-like cell death has also been described in unicellular organisms, including intracellular pathogens. From an overall population perspective, the induction of apoptosis could be employed by the pathogens to evade immune responses. Evidence has supported the idea that apoptosis contributes to survival of the overall population by the fact that phagocytosis of apoptotic-like parasites induces production of anti-inflammatory mediators, likely to silence phagocytes enabling the intracellular survival of viable pathogens, in particular when macrophages are the host cell.

To circumvent identification and elimination through the immune system and secure survival, intracellular pathogens have evolved strategies to silence their host immune response. Apoptotic mimicry is a strategy used by many obligate intracellular pathogens to enter and infect immune cells as well as spread to distant sites. Apoptotic mimicry involves the self-cloaking of pathogens with PS+ envelopes derived from the membranes of infected cells. PS+ envelopes mimic host apoptotic cells/bodies, allowing the enclosed pathogens to escape detection by the immune system and infect other target cells after gaining intracellular entry via efferocytosis (the process by which dying or dead cells are removed by phagocytosis). Intracellular pathogens known to use PS+ envelopes during infection include, for example, bacterial pathogens such as *L. monocytogenes*, *Mycobacterium marinum*, and *Chlamydia trachomatis*.

Parasites, such as *Leishmania*, also use PS exposure to prevent and effective immune response through an alternative form of apoptotic mimicry. In *Leishmania* infection, a small minority of single cell parasites undergo an apoptotic like cell death to suppress T-cell anti-pathogen responses to permit the survival of the overall population. Phagocytosis of apoptotic-like parasites induces production of anti-inflammatory mediators, likely to silence the host immune responses, and enabling the intracellular survival of viable parasites. Parasites including *Trypanosoma cruzi* use this same mechanism to avoid T-cell response and PS exposure by *Toxoplasma gondii* permits its survival and propagation within macrophages.

Methods of blocking intracellular pathogens are of great clinical interest, and are addressed herein.

SUMMARY OF THE INVENTION

Methods are provided for treating an individual infected with an intracellular pathogen, by administering an effective dose of an annexin V agent. Certain pathogens evade host immune defenses by enveloping themselves within membranes containing high levels of exofacial phosphatidylserine (PS) at different phases of infection. These PS+ membrane envelopes can allow entry into a target host immune cell, and the silencing of an effective host immune response. Without being bound by any theory, the subject methods indicate that exogenously administered annexin V has an anti-intracellular pathogen effect through the binding of PS on intracellular pathogen cells, thereby blocking regulatory T cell immunosuppression of the immune system. The methods of the invention provide a well-tolerated blockade of PS, that enhances host immune response to intracellular pathogen.

Methods are provided for treatment of an intracellular pathogen infection by administering an effective dose of an agent that blocks the binding sites of phosphatidylserine (PS) on the pathogen cell surface. In some embodiments the blocking agent is a protein that binds to PS, thereby competitively masking, or blocking, the available binding sites. Annexin V is an endogenous human protein which binds to exofacial PS with a high nanomolar affinity and may be used for this purpose. Polypeptides of interest for administration include, without limitation, annexin V protein and PS binding fragments derived therefrom, and include wild-type and mutant (e.g. annexin V-128) sequences. Administration of an effective dose of annexin V blocks, or masks, the surface PS thereby reducing the spread of the pathogen.

Embodiments of the invention include treating a mammalian subject, including without limitation dog, cat, pig, sheep, cow, horse, human, etc. In particular embodiments the methods are used in the treatment of chronic pathogen infections, for example including but not limited to intracellular bacterial infections, e.g. *Mycobacterium, Chiamydophila, Ehrlichia, Rickettsia, Brucella, Legionella, Francisella, Listeria, Coxiella, Neisseria, Salmonella, Yersinia* sp, etc.; and intracellular protozoan pathogens, e.g. *Plasmodium* sp, *Trypanosoma* sp., *Giardia* sp., *Toxoplasma* sp., *Leishmania* sp., etc. Treatment of *Listeria monocytogenes* infection is of particular interest.

In some embodiments of the invention, an effective dose of annexin V protein is administered, e.g. by parenteral administration, locally or systemically to an individual with intracellular pathogen. In some embodiments the administration is performed by continuous systemic infusion. In some embodiments such continuous systemic infusion comprises intraperitoneal infusion. In some embodiments, an osmotic pump is deployed.

In some embodiments of the invention, an effective dose of annexin V protein is administered parenterally to an individual diagnosed with intracellular pathogen, where the administration may be i.v., i.p., or the like, in particular intraperitoneal continuous infusion. The effective dose in a human may be up to about 50 μg/kg, up to about 100 μg/kg, up to about 250 μg/kg, up to about 500 μg/kg, up to about 750 μg/kg, up to about 1 mg/kg, up to about 1.5 mg/kg, up to about 2 mg/kg, up to about 5 mg/kg, up to about 7.5 mg/kg, up to about 10 mg/kg, up to about 20 mg/kg.

The effective dose of annexin V may be combined with other treatment modalities. In some embodiments a synergistic effect is observed when the annexin V therapy is combined with antibiotics.

In some embodiments, the Annexin V protein is administered in a manner that provides for prolonged blood clearance of the protein, for example where the half-life of the protein in circulation is at least about 30 minutes, at least about 1 hour, at least about 1.5 hours, at least about 2 hours, at least about 2.5 hours, at least about 3 hours or more. In some embodiments the manner of administration is intraperitoneal injection, or osmotic pump. In other embodiments the route of administration is intravenous injection over an extended period of time, for example where a daily dosage as described above is delivered over a period of up to 30 minutes, up to one hour, up to 2 hours, up to 4 hours, up to 6 hours, up to 8 hours, up to 12 hours, up to 16 hours, up to 24 hours.

Another aspect of the present invention relates to the use of an annexin V agent in the manufacture of a medicament to treat infection with intracellular pathogens.

Still another aspect of the present invention provides a kit to treat infection with intracellular pathogens. The kit includes a therapeutic annexin V agent, which blocks PS on the surface of intracellular pathogen cell surface in an amount sufficient to reduce disease. The kit may also include antibiotics. The kit may also instructions for use, reagents for monitoring intracellular pathogen growth, and the like.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

FIG. 4. Total BLI Counts (#Photons collected over 30 seconds)

DETAILED DESCRIPTION OF THE INVENTION

Figure 1A:
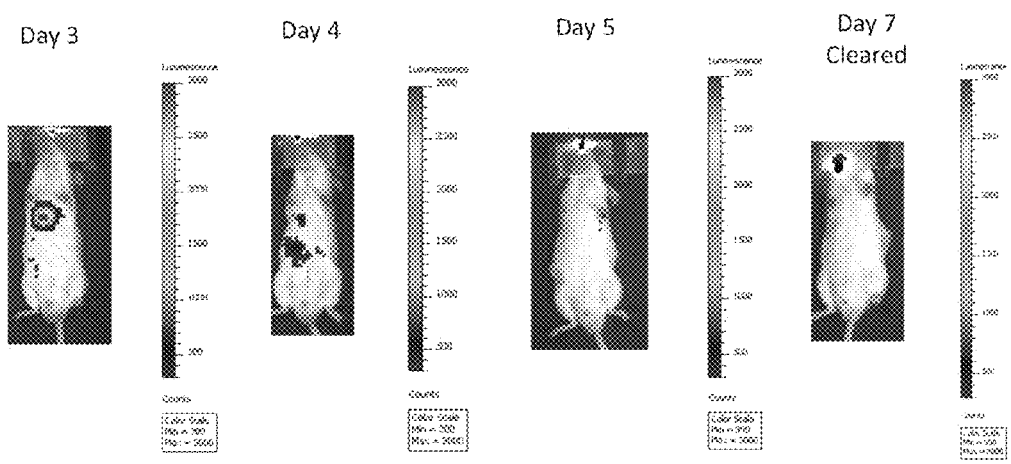
FIG. 1A-1B show the effect of annexin V treatment on the spread of *Listeria monocytogenes* infection.
Figure 1B:
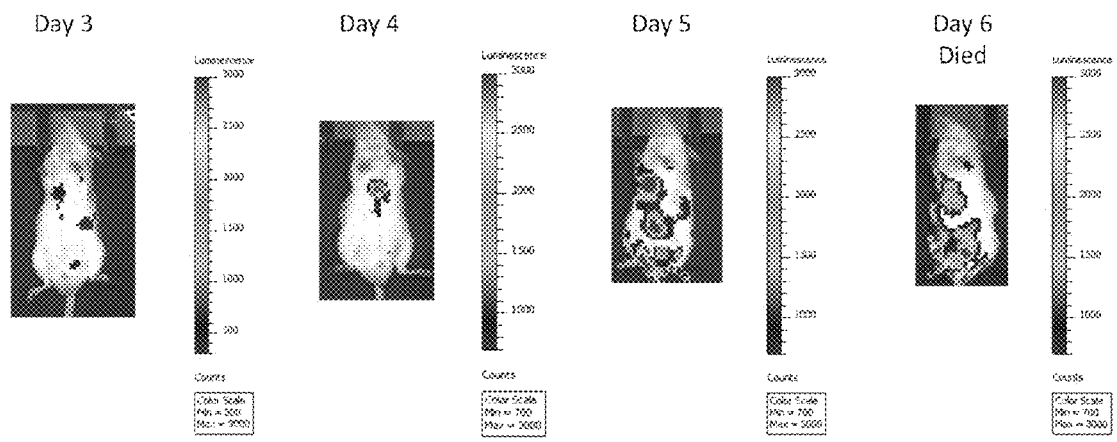
Figure 2:
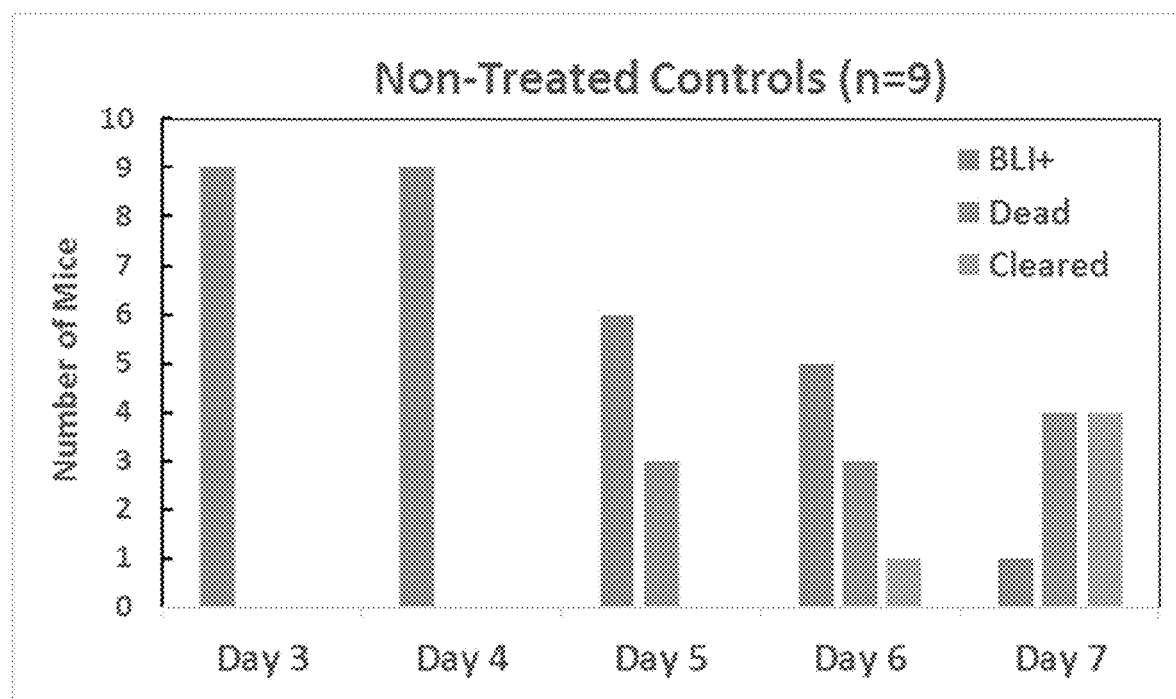
FIG. 2. Untreated Controls ($4 \times 10^5$ cfu of *Listeria* injected Day 0).
Figure 3:
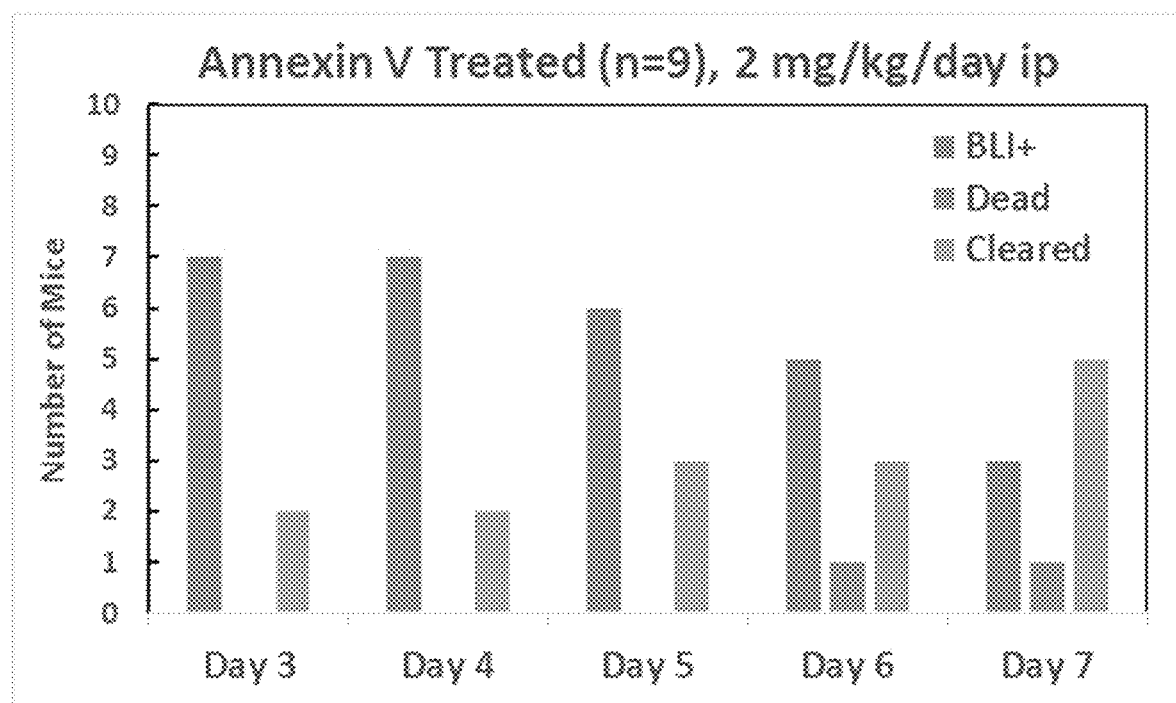
FIG. 3. Annexin V Treated 2 mg/kg ip starting on Day 0. ($4 \times 10^5$ cfu of *Listeria* injected Day 0)

The invention provides methods for treating infections with an intracellular pathogen in a mammalian subject. The methods of the invention comprise administering to the subject an effective amount of an agent that provides annexin V binding activity, to suppress or prevent initiation, progression, or relapses of infectious disease. In this invention, administering the instant compositions can be effected or performed using any of the various methods and delivery systems known to those skilled in the art. The administering can be performed, for example, intravenously, via implant, transmucosally, transdermally, intramuscularly, intrathecally, and subcutaneously. The delivery systems described below, which employ a number of routinely used pharmaceutical carriers, are only representative of the many embodiments envisioned for administering the annexin V compositions.

The terms "treatment", "treating", "treat" and the like are used herein to generally refer to obtaining a desired pharmacologic and/or physiologic effect. The effect can be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom. Those in need of treatment include those already with an infection as well as those in which an infection is to be prevented. As such, a therapeutic treatment is one in which the subject is infected prior to administration and a prophylactic treatment is one in which the subject is not infected prior to administration. In some embodiments, the subject is suspected of being infected prior to administration. In some embodiments, the subject has an increased risk of infection prior to administration. In some embodiments, the subject is suspected of being at increased risk of infection prior to administration.

The terms "recipient", "individual", "subject", "host", and "patient", are used interchangeably herein and refer to any mammalian subject for whom diagnosis, treatment, or therapy is desired, particularly humans. "Mammal" for purposes of treatment refers to any animal classified as a mammal, including humans, domestic and farm animals, and zoo, sports, or pet animals, such as dogs, horses, cats, cows, sheep, goats, pigs, etc. Preferably, the mammal is human.

A "therapeutically effective dose" or "therapeutic dose" is an amount sufficient to effect desired clinical results (i.e., achieve therapeutic efficacy). A therapeutically effective dose can be administered in one or more administrations. For purposes of this invention, a therapeutically effective dose of Annexin V is an amount that is sufficient to palliate, ameliorate, stabilize, reverse, prevent, slow or delay the progression of the disease state (e.g., intracellular pathogen) by increasing innate immune responsiveness. Thus, a therapeutically effective dose of Annexin V agent binds to phosphatidylserine on an intracellular pathogen cell, thereby blocking the suppression of immune responsiveness, e.g. by a regulatory T cell, a phagocytic cells, an NK cell, and the like.

As used herein, a "target cell" is typically an infected cell. Usually a target cell is a mammalian cell, for example a human cell.

As used herein, the term "infection" refers to any state in at least one cell of an organism (i.e., a subject) is infected by an infectious agent. As used herein, the term "infectious agent" refers to a foreign biological entity, i.e. a pathogen, that utilizes phosphatidylserine to decrease host immune responses, e.g. by apoptosis or apoptotic mimicry. Usually the infectious agent is an intracellular pathogen, e.g. an intracellular bacterium or protozoan. Infectious diseases are disorders caused by infectious agents. Some infectious agents cause no recognizable symptoms or disease under certain conditions, but have the potential to cause symptoms or disease under changed conditions.

"Suitable conditions" shall have a meaning dependent on the context in which this term is used. That is, when used in connection with an antibody, the term shall mean conditions that permit an antibody to bind to its corresponding antigen. When this term is used in connection with nucleic acid hybridization, the term shall mean conditions that permit a nucleic acid of at least 15 nucleotides in length to hybridize to a nucleic acid having a sequence complementary thereto. When used in connection with contacting an agent to a cell, this term shall mean conditions that permit an agent capable of doing so to contact an entity on the cell surface and bind to it. In one embodiment, the term "suitable conditions" as used herein means physiological conditions.

The terms "specific binding," "specifically binds," and the like, refer to non-covalent or covalent preferential binding to a molecule relative to other molecules or moieties in a solution or reaction mixture (e.g., annexin V specifically binds to phosphatidylserine). In some embodiments, the affinity of one molecule for another molecule to which it specifically binds is characterized by a $K_D$ (dissociation constant) of $10^{-5}$ M or less (e.g., $10^{-6}$ M or less, $10^{-7}$ M or less, $10^{-8}$ M or less, $10^{-9}$ M or less, $10^{-10}$ M or less, $10^{-11}$ M or less, $10^{-12}$ M or less, $10^{-13}$ M or less, $10^{-14}$ M or less, $10^{-15}$ M or less, or $10^{-16}$ M or less). "Affinity" refers to the strength of binding, increased binding affinity being correlated with a lower $K_D$.

The term "specific binding member" as used herein refers to a member of a specific binding pair (i.e., two molecules, usually two different molecules, where one of the molecules, e.g., a first specific binding member, through non-covalent means specifically binds to the other molecule, e.g., a second specific binding member).

The terms "polypeptide," "peptide" and "protein" are used interchangeably herein to refer to a polymer of amino acid residues. The terms also apply to amino acid polymers in which one or more amino acid residue is an artificial chemical mimetic of a corresponding naturally occurring amino acid, as well as to naturally occurring amino acid polymers and non-naturally occurring amino acid polymer.

The term "sample" with respect to a patient encompasses blood and other liquid samples of biological origin, solid tissue samples such as a biopsy specimen or tissue cultures or cells derived or isolated therefrom and the progeny thereof. The definition also includes samples that have been manipulated in any way after their procurement, such as by treatment with reagents; washed; or enrichment for certain cell populations, such as intracellular pathogen cells. The definition also includes samples that have been enriched for particular types of molecules, e.g., nucleic acids, polypeptides, etc.

The term "biological sample" encompasses a clinical sample, and also includes tissue obtained by surgical resection, tissue obtained by biopsy, cells in culture, cell supernatants, cell lysates, tissue samples, organs, bone marrow, blood, plasma, serum, and the like. A "biological sample" includes a sample comprising target cells or normal control cells or suspected of comprising such cells or biological fluids derived therefrom (e.g., a pathogen, an infected cell, etc.), e.g., a sample comprising polynucleotides and/or polypeptides that is obtained from such cells (e.g., a cell lysate or other cell extract comprising polynucleotides and/or polypeptides). A biological sample comprising an inflicted cell from a patient can also include non-inflicted cells.

Efferocytosis. The process by which professional and nonprofessional phagocytes dispose of apoptotic cells in a rapid and efficient manner. Efferocytosis involves a number of molecules, including ligands on the apoptotic cells, e.g. phosphatidylserine; receptors on the efferocyte; soluble ligand-receptor bridging molecules; and so-called "find-me" and "don't-eat-me" molecules, e.g., lysosphospholipids and CD47, the expression of which by dying cells is altered to attract nearby phagocytes. By clearing apoptotic cells at a relatively early stage of cell death, when the cell plasma and organelle membranes are still intact, postapoptotic, or "secondary", necrosis is prevented. Prevention of cellular necrosis, in turn, prevents the release of potentially damaging intracellular molecules into the extracellular milieu, including molecules that can stimulate inflammatory, proatherosclerotic and/or autoimmune responses.

By "manipulating efferocytosis" is meant an up-regulation or a down-regulation in efferocytosis of a targeted cell by at least about 10%, or up to 20%, or 50%, or 70% or 80% or up to about 90% compared to level of efferocytosis observed in absence of intervention.

The terms "phagocytic cells" and "phagocytes" are used interchangeably herein to refer to a cell that is capable of phagocytosis. There are three main categories of phagocytes: macrophages, mononuclear cells (histiocytes and monocytes); polymorphonuclear leukocytes (neutrophils) and dendritic cells. However, "non-professional" cells are also known to participate in efferocytosis.

Annexin-V (PAP-I, lipocortin-V) binds to negatively charged phospholipids with high affinity, for example having a Kd in the $10^{-9}$ to $10^{-10}$ M range. Annexin V forms a shield around negatively-charged phospholipid molecules. This formation blocks the entry of phospholipids into coagulation (clotting) reactions, and prevents interaction of the phospholipid with immunoregulatory cells. The genetic sequence of human annexin V can be accessed at Genbank, NM_001154. The crystal and molecular structure is described in Romisch and Paques (1992) J. Mol. Biol. 223 (3), 683-704. Annexin V polypeptides or biologically active fragments and variants thereof, and the like, are used in the treatment of intracellular pathogen. In some embodiments the annexin V has a wild-type or native sequence. In other embodiments the annexin V is a annexin V-128 mutant protein.

Active fragments of annexin V share a functional or binding property with full length annexin V. For example, epitopic fragments of annexin V bind to a monoclonal antibody that binds to full length annexin V. "Activity" of annexin V shall mean any binding function performed by that protein.

Annexin V polypeptides, which can be used in the methods of the invention, comprise at least about 50 contiguous amino acids, usually at least about 100 contiguous amino acids, at least about 150 contiguous amino acids, at least about 200 contiguous amino acids, at least about 250 contiguous amino acids, and which may include up to 320 contiguous amino acids of an annexin V protein, including without limitation human annexin V protein, or modifications thereof, and may further include fusion polypeptides as known in the art in addition to the provided sequences. The Annexin V sequence may be from any mammalian or avian species, e.g. primate sp., particularly humans; rodents, including mice, rats and hamsters; rabbits; equines, bovines, canines, felines; etc. Of particular interest are the human proteins.

In some embodiments of the invention, the annexin V protein, or a functional fragment thereof is administered to a patient. Annexin V polypeptides useful in this invention also include derivatives, variants, and biologically active fragments of naturally occurring annexin V polypeptides, and the like. A "variant" polypeptide means a biologically active polypeptide as defined below having less than 100% sequence identity with a native sequence polypeptide. Such variants include polypeptides wherein one or more amino acid residues are added at the N- or C-terminus of, or within, the native sequence; from about one to forty amino acid residues are deleted, and optionally substituted by one or more amino acid residues; and derivatives of the above polypeptides, wherein an amino acid residue has been covalently modified so that the resulting product has a non-naturally occurring amino acid. Ordinarily, a biologically active variant will have an amino acid sequence having at least about 90% amino acid sequence identity with a native sequence polypeptide, preferably at least about 95%, more preferably at least about 99%.

The sequence of annexin V peptides as described above may be altered in various ways known in the art to generate targeted changes in sequence. The sequence changes may be substitutions, insertions or deletions. Such alterations may be used to alter properties of the protein, by affecting the stability, specificity, etc. Techniques for in vitro mutagenesis of cloned genes are known. Examples of protocols for scanning mutations may be found in Gustin et al., Biotechniques 14:22 (1993); Barany, Gene 37:111-23 (1985); Colicelli et al., Mol Gen Genet 199:537-9 (1985); and Prentki et al., Gene 29:303-13 (1984). Methods for site specific mutagenesis can be found in Sambrook et al., Molecular Cloning: A Laboratory Manual, CSH Press 1989, pp. 15.3-15.108; Weiner et al., Gene 126:35-41 (1993); Sayers et al., Biotechniques 13:592-6 (1992); Jones and Winistorfer, Biotechniques 12:528-30 (1992); Barton et al., Nucleic Acids Res 18:7349-55 (1990); Marotti and Tomich, Gene Anal Tech 6:67-70 (1989); and Zhu Anal Biochem 177:120-4 (1989).

The proteins may be joined to a wide variety of other oligopeptides or proteins for a variety of purposes. By providing for expression of the subject peptides, various post-expression modifications may be achieved. For example, by employing the appropriate coding sequences, one may provide farnesylation or prenylation. The peptides may be PEGylated, where the polyethyleneoxy group provides for enhanced lifetime in the blood stream. The peptides may also be combined with other proteins in a fusion protein, typically where the two proteins are not normally joined, such as the Fc of an IgG isotype, which may be complement binding, with a toxin, such as ricin, abrin, diphtheria toxin, or the like, or with specific binding agents that allow targeting to specific moieties on a target cell.

The annexin V may be fused to another polypeptide to provide for added functionality, e.g. to increase the in vivo stability. Generally such fusion partners are a stable plasma protein, which may, for example, extend the in vivo plasma half-life of the Annexin V when present as a fusion, in particular wherein such a stable plasma protein is an immunoglobulin constant domain.

The annexin V for use in the subject methods may be produced from eukaryotic or prokaryotic cells, or may be synthesized in vitro. Where the protein is produced by prokaryotic cells, it may be further processed by unfolding, e.g. heat denaturation, DTT reduction, etc. and may be further refolded, using methods known in the art. By using synthesizers, naturally occurring amino acids may be substituted with unnatural amino acids. The particular sequence and the manner of preparation will be determined by convenience, economics, purity required, and the like.

Modifications of interest that do not alter primary sequence include chemical derivatization of polypeptides, e.g., acylation, acetylation, carboxylation, amidation, etc. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine.

Also included in the subject invention are polypeptides that have been modified using ordinary molecular biological techniques and synthetic chemistry so as to improve their resistance to proteolytic degradation or to optimize solubility properties or to render them more suitable as a therapeutic agent. Analogs of such polypeptides include those containing residues other than naturally occurring L-amino acids, e.g. D-amino acids or non-naturally occurring synthetic amino acids. D-amino acids may be substituted for some or all of the amino acid residues.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

The polypeptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

In one embodiment of the invention, the annexin V polypeptide consists essentially of a polypeptide sequence of around about 320 amino acids in length and having a sequence of an annexin V peptide as described above. By "consisting essentially of" in the context of a polypeptide described herein, it is meant that the polypeptide is composed of the annexin V sequence, which sequence is optionally flanked by one or more amino acid or other residues that do not materially affect the basic characteristic(s) of the polypeptide.

As used herein, the term "administration" refers to the administration of a composition to a subject or system. Administration to an animal subject (e.g., to a human) may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intravenous, intraventricular, within a specific organ (e. g. intrahepatic), mucosal, nasal, oral, rectal, subcutaneous, sublingual, topical, tracheal (including by intratracheal instillation), transdermal, vaginal and vitreal. In some embodiments, administration may involve intermittent dosing. In some embodiments, administration may involve continuous dosing (e.g., perfusion) for at least a selected period of time. As is known in the art, antibody therapy is commonly administered parenterally (e.g., by intravenous or subcutaneous injection).

As used herein, the term "combination therapy" refers to those situations in which a subject is simultaneously exposed to two or more therapeutic regimens (e.g., two or more therapeutic agents). In some embodiments, two or more agents may be administered simultaneously; in some embodiments, such agents may be administered sequentially; in some embodiments, such agents are administered in overlapping dosing regimens.

As used herein, the term "dosing regimen" refers to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount In some embodiments, a dosing regimen is correlated with a desired or beneficial outcome when administered across a relevant population (i.e., is a therapeutic dosing regimen).

Unless otherwise apparent from the context, all elements, steps or features of the invention can be used in any combination with other elements, steps or features.

General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998). Reagents, cloning vectors, and kits for genetic manipulation referred to in this disclosure are available from commercial vendors such as BioRad, Stratagene, Invitrogen, Sigma-Aldrich, and ClonTech.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in an underlying DNA sequence without affecting the protein sequence. Moreover, due to biological functional equivalency considerations, changes, particularly conservative changes, can be made in protein structure without affecting the biological action in kind or amount. All such modifications are intended to be included within the scope of the appended claims.

Methods

Methods are provided for treating or reducing infection, including without limitation intracellular bacterial and protozoan infections, by blocking PS on the pathogen surface, thereby preventing suppression of host immune responses. Such methods include administering to a subject in need of treatment a therapeutically effective amount or an effective dose of annexin V, including without limitation combinations of the reagent with another drug. In one aspect, the present invention discloses a method for treating intracellular pathogen by reducing immunosuppression associated with intracellular pathogen cell growth. The methods of the invention administer an effective dose of annexin V to block or mask PS on the surface of a pathogen cell, and to thereby disrupt undesirable interactions between pathogen cells and host cells that are targets for infection, and/or immunoregulatory cells.

In some embodiments the infection is a chronic infection, i.e. an infection that is not cleared by the host immune system within a period of up to 1 week, 2 weeks, etc. In some cases, chronic infections, for example certain intracellular bacteria or protozoan pathogens, result from a pathogen cell residing within a host cell.

The effective daily dose of an annexin V agent, e.g. human annexin V protein, in a human may be up to about 50 µg/kg, up to about 100 µg/kg, up to about 250 µg/kg, up to about 500 µg/kg, up to about 750 µg/kg, up to about 1 mg/kg, up to about 1.5 mg/kg, up to about 2 mg/kg, up to about 5 mg/kg, up to about 7.5 mg/kg, up to about 10 mg/kg, up to about 20 mg/kg. The administration of a therapeutically effective dose of an annexin V agent can be achieved in a number of different ways Suitable administration of a therapeutically effective dose can entail administration of a single dose, or can entail administration of doses daily, semi-weekly, weekly, once every two weeks, once a month, annually, etc., including continuous infusion.

Microbes of interest, but not limited to the following, include: *Yersinia* sp., e.g. *Y. pestis*, *Y. pseudotuberculosis*, *Y enterocolitica*; *Franciscella* sp.; *Pasteurella* sp.; *Vibrio* sp., e.g. *V. cholerae*, *V. parahemolyticus*; *Legionella* sp., e.g. *L. pneumophila*; *Listeria* sp., e.g. *L. monocytogenes*; *Mycoplasma* sp., e.g. *M. hominis*, *M. pneumoniae*; *Mycobacterium* sp., e.g. *M. tuberculosis*, *M. leprae*; *Rickettsia* sp., e.g. *R. rickettsii*, *R. typhi*; *Chlamydia* sp., e.g. *C. trachomatis*, *C. pneumoniae*, *C. psittaci*; *Helicobacter* sp., e.g. *H. pylori*, etc. Also included are intracellular protozoan pathogens, e.g. *Plasmodium* sp, *Trypanosoma* sp., *Giardia* sp., *Toxoplasma* sp., *Leishmania* sp., etc. Bacterial pathogens of particular interest include *Listeria monocytogenes*, *Mycobacterium marinum*, and *Chlamydia trachomatis*. Protozoan pathogens of particular interest include *Trypanosoma cruzi*, *Toxoplasma gondii*, *Leishmania* sp., including *L. major*, *L. tropica*, *L. aethiopica*, *L. braziliensis*, *L. donovani*; and *Plasmodium falciparum*.

An infection treated with the methods of the invention generally involves a pathogen with at least a portion of its life-cycle within a host cell, i.e. an intracellular phase, and usually involve an apoptosis or apoptotic mimicry mechanism utilized by the pathogen. The methods of the invention provide for a more effective resistance to infection, and immune response to the pathogen, relative to the response in the absence of treatment.

In some embodiments, the methods of the invention involve diagnosis of a patient as suffering from a pathogenic intracellular infection; or selection of a patient previously diagnosed as suffering from a pathogenic intracellular infection; treating the patient with a regimen of annexin V therapy, optionally in combination with an additional therapy; and monitoring the patient for efficacy of treatment.

Monitoring may measure clinical indicia of infection, e.g. fever, white blood cell count, etc., and/or direct monitoring for presence of the pathogen.

Treatment may be combined with other active agents. The combination may provide for an effect on intracellular pathogen growth or survival that is synergistic relative to the effect of the individual therapies, that is the effect of annexin V or a checkpoint inhibitor as a monotherapy. Classes of antibiotics include penicillins, e.g. penicillin G, penicillin V, methicillin, oxacillin, carbenicillin, nafcillin, ampicillin, etc.; penicillins in combination with β-lactamase inhibitors, cephalosporins, e.g. cefaclor, cefazolin, cefuroxime, moxalactam, etc.; carbapenems; monobactams; aminoglycosides; tetracyclines; macrolides; lincomycins; polymyxins; sulfonamides; quinolones; cloramphenical; metronidazole; spectinomycin; trimethoprim; vancomycin; etc. Cytokines may also be included, e.g. interferon γ, tumor necrosis factor α, interleukin 12, etc. Antiparasitic agents include nitroimidazole, e.g. metronidazole; ivermectin, tinidazole; trimethoprim and sulphamethoxazole; etc.

A pathogen infection can be monitored during and after treatment by the methods of the present invention. Clinical efficacy can be measured by any method known in the art. In some embodiments, clinical efficacy of the subject treatment method is determined by measuring the clinical benefit rate (CBR).

Pharmaceutical Compositions.

Suitable annexin V agents can be provided in pharmaceutical compositions suitable for therapeutic use, e.g. for human treatment. In some embodiments, pharmaceutical compositions of the present invention include one or more therapeutic entities of the present invention or pharmaceutically acceptable salts, esters or solvates thereof. In some other embodiments, the use of an annexin V agent includes use in combination with another therapeutic agent (e.g., another anti-intracellular pathogen agent). Therapeutic formulations comprising one or more annexin V agents of the invention are prepared for storage by mixing the agent having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. The agent composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The annexin V agent can be administered by any suitable means, particularly parenteral parenteral. Parenteral infusions include intramuscular, intravenous (bollus or slow drip), intraarterial, intraperitoneal, intrathecal, intraintracellular pathogen, or subcutaneous administration.

The annexin V agent need not be, but is optionally formulated with one or more agents that potentiate activity, or that otherwise increase the therapeutic effect. These are generally used in the same dosages and with administration routes as used hereinbefore or about from 1 to 99% of the heretofore employed dosages.

An annexin V agent is often administered as a pharmaceutical composition comprising an active therapeutic agent and another pharmaceutically acceptable excipient. The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

In still some other embodiments, pharmaceutical compositions can also include large, slowly metabolized macromolecules such as proteins, polysaccharides such as chitosan, polylactic acids, polyglycolic acids and copolymers (such as latex functionalized Sepharose™ agarose, cellulose, and the like), polymeric amino acids, amino acid copolymers, and lipid aggregates (such as oil droplets or liposomes).

A carrier may bear the agents in a variety of ways, including covalent bonding either directly or via a linker group, and non-covalent associations. Suitable covalent-bond carriers include proteins such as albumins, peptides, and polysaccharides such as aminodextran, each of which have multiple sites for the attachment of moieties. A carrier may also bear annexin V by non-covalent associations, such as non-covalent bonding or by encapsulation. The nature of the carrier can be either soluble or insoluble for purposes of the invention. Those skilled in the art will know of other suitable carriers or will be able to ascertain such, using routine experimentation.

Acceptable carriers, excipients, or stabilizers are non-toxic to recipients at the dosages and concentrations employed, and include buffers such as phosphate, citrate, and other organic acids; antioxidants including ascorbic acid and methionine; preservatives (such as octadecyidimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Formulations to be used for in vivo administration must be sterile. This is readily accomplished by filtration through sterile filtration membranes.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Carriers and linkers specific for radionuclide agents include radiohalogenated small molecules and chelating compounds. A radionuclide chelate may be formed from chelating compounds that include those containing nitrogen and sulfur atoms as the donor atoms for binding the metal, or metal oxide, radionuclide.

Radiographic moieties for use as imaging moieties in the present invention include compounds and chelates with relatively large atoms, such as gold, iridium, technetium, barium, thallium, iodine, and their isotopes. It is preferred that less toxic radiographic imaging moieties, such as iodine or iodine isotopes, be utilized in the methods of the invention. Such moieties may be conjugated to the annexin V agent through an acceptable chemical linker or chelation carrier. Positron emitting moieties for use in the present invention include $^{18}F$, which can be easily conjugated by a fluorination reaction with the annexin V agent.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. Langer, Science 249: 1527, 1990 and Hanes, Advanced Drug Delivery Reviews 28: 97-119, 1997. The agents of this invention can be administered in the form of a depot injection or implant preparation which can be formulated in such a manner as to permit a sustained or pulsatile release of the active ingredient. The pharmaceutical compositions are generally formulated as sterile, substantially isotonic and in full compliance with all Good Manufacturing Practice (GMP) regulations of the U.S. Food and Drug Administration.

Toxicity of the annexin V agents can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in further optimizing a therapeutic dosage range and/or a priming dosage range for use in humans. The exact formulation, route of administration and dosage can be chosen by the individual physician in view of the patient's condition.

Kits

Also provided are kits for use in the methods. The subject kits include an annexin V agent, e.g. full-length human annexin V protein or active fragment derived therefrom. In some embodiments, the agent is provided in a dosage form (e.g., a therapeutically effective dosage form). In some embodiments, annexin V is provided in two or more different dosage forms (e.g., two or more different therapeutically effective dosage forms). In the context of a kit, an agent can be provided in liquid or sold form in any convenient packaging (e.g., stick pack, dose pack, etc.).

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), flash drive, and the like, on which the information has been recorded. Yet another form of these instructions that may be present is a website address which may be used via the internet to access the information at a removed site. The kit may further comprise imaging agents for detection and imaging of PS positive intracellular pathogen cells suitable for treatment with the methods of the invention.

The invention now being fully described, it will be apparent to one of ordinary skill in the art that various changes and modifications can be made without departing from the spirit or scope of the invention.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

Example 1

$5 \times 10^5$/mL of *Listeria* (-luc expressing for daily BLI imaging) bacteria growing at log phase were injected via tail vein into two groups of CD-1 female mice (n=5 each) 12 weeks in age on Day 0. On Day 1 all 10 mice were imaged. Then the five experimental group mice were injected with a single ip dose of stock annexin V at 2 mg/kg ip followed up by daily ip doses of annexin V×4 days.

It took several days for treated mice to clear *Listeria* (3 of 5) as confirmed by BLI. Furthermore, after two to three doses of annexin V treated mice regained a healthy appearance and demonstrated normal behavior despite a sizable bacterial load in the liver and spleen of one mouse. A single annexin V treated mouse died on Day 3 likely due to the intrinsic variability in the *Listeria* infection model. The 4 surviving treated mice were euthanized on Day 6, all in apparent health as observed clinically.

2 of 5 untreated infected controls died; one on Day 4 and the other Day 5. All untreated mice (5 of 5) had progression of bacterial load (by BLI) and clear clinical illness until death or euthanization on Day 6.

TABLE 1

Summary of BLI Activity and Survival for
Annexin V Treated and Control Listeria Infected Mice

| | # of mice | # of mice | # of mice | # of mice | # of mice |
|---|---|---|---|---|---|
| Control | | | | | |
| BLI+ | 9 | 9 | 6 | 5 | 1 |
| Dead | 0 | 0 | 3 | 3 | 4 |
| Cleared | 0 | 0 | 0 | 1 | 4 |
| | Day 3 | Day 4 | Day 5 | Day 6 | Day 7 |
| Annexin V Rx | | | | | |
| BLI+ | 7 | 7 | 6 | 5 | 3 |
| Dead | 0 | 0 | 0 | 1 | 1 |
| Cleared | 2 | 2 | 3 | 3 | 5 |
| | Day 3 | Day 4 | Day 5 | Day 6 | Day 7 |

What is claimed is:

1. A method of treating a human for infection with *Listeria monocytogenes*, the method comprising:
parenteral administration to a subject infected with *Listeria monocytogenes* of an effective dose of human annexin V protein wherein the administering is performed by a route that provides for a circulating half-life of at least about 1 hour.

2. The method of claim 1, wherein the subject has been previously diagnosed as having *Listeria monocytogenes*.

3. The method of claim 1, further comprising the step of monitoring the subject for clinical signs of infection or for presence of *Listeria monocytogenes*, and if the infection is present, then re-administering the annexin V protein to the subject.

4. The method of claim 1, wherein the effective dose is from about 50 μg/kg to about 20 mg/kg.

5. The method of claim 1, wherein administration is intraperitoneal.

6. The method of claim 1, wherein administering is performed by intravenous administration over a period of at least 4 hours.

7. The method of claim 1, wherein the effective dose is administered at least twice.

8. The method of claim 1, wherein the effective dose is administered in a combination therapy with a second agent.

* * * * *